Figure 1:
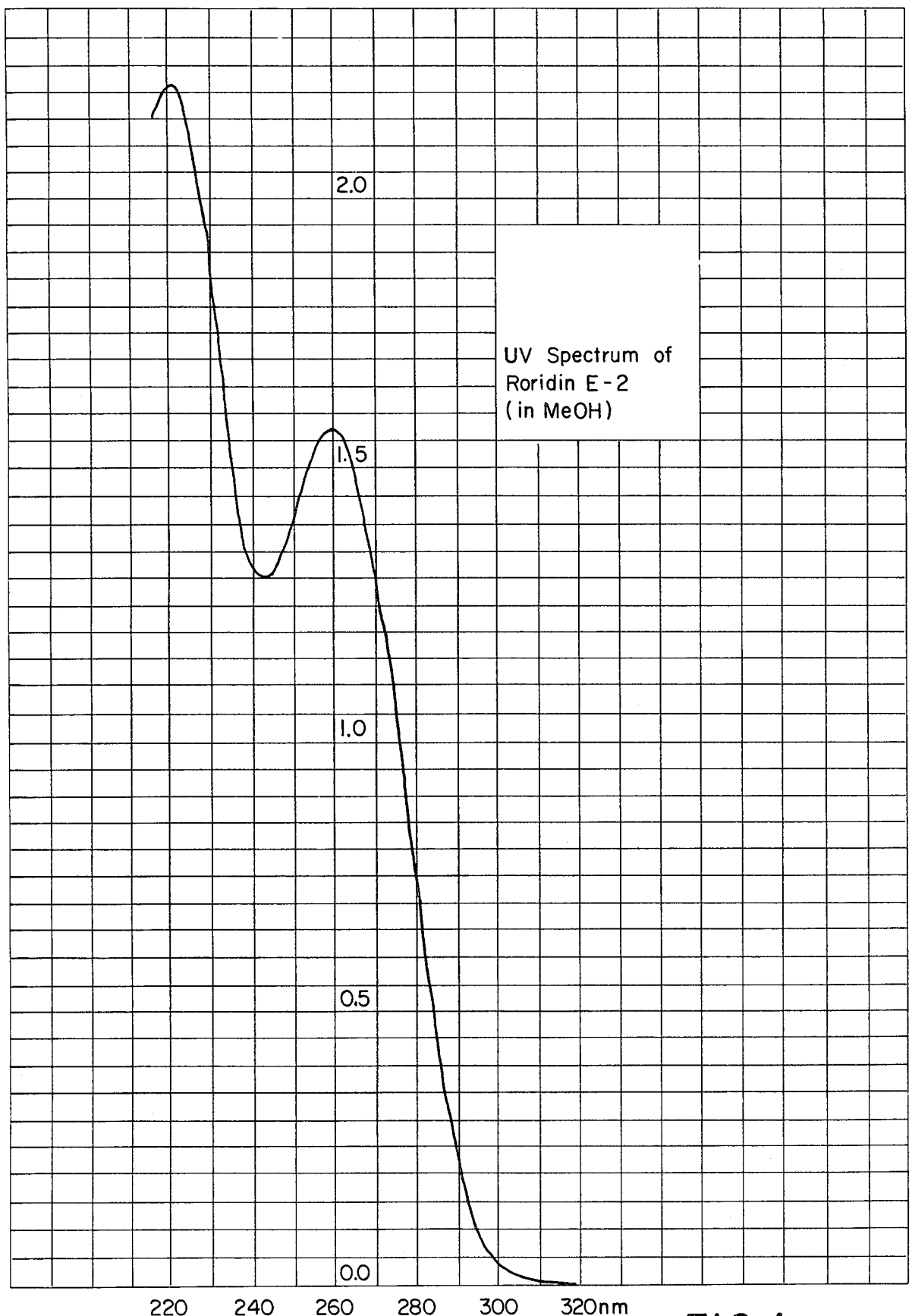
Figure 2:
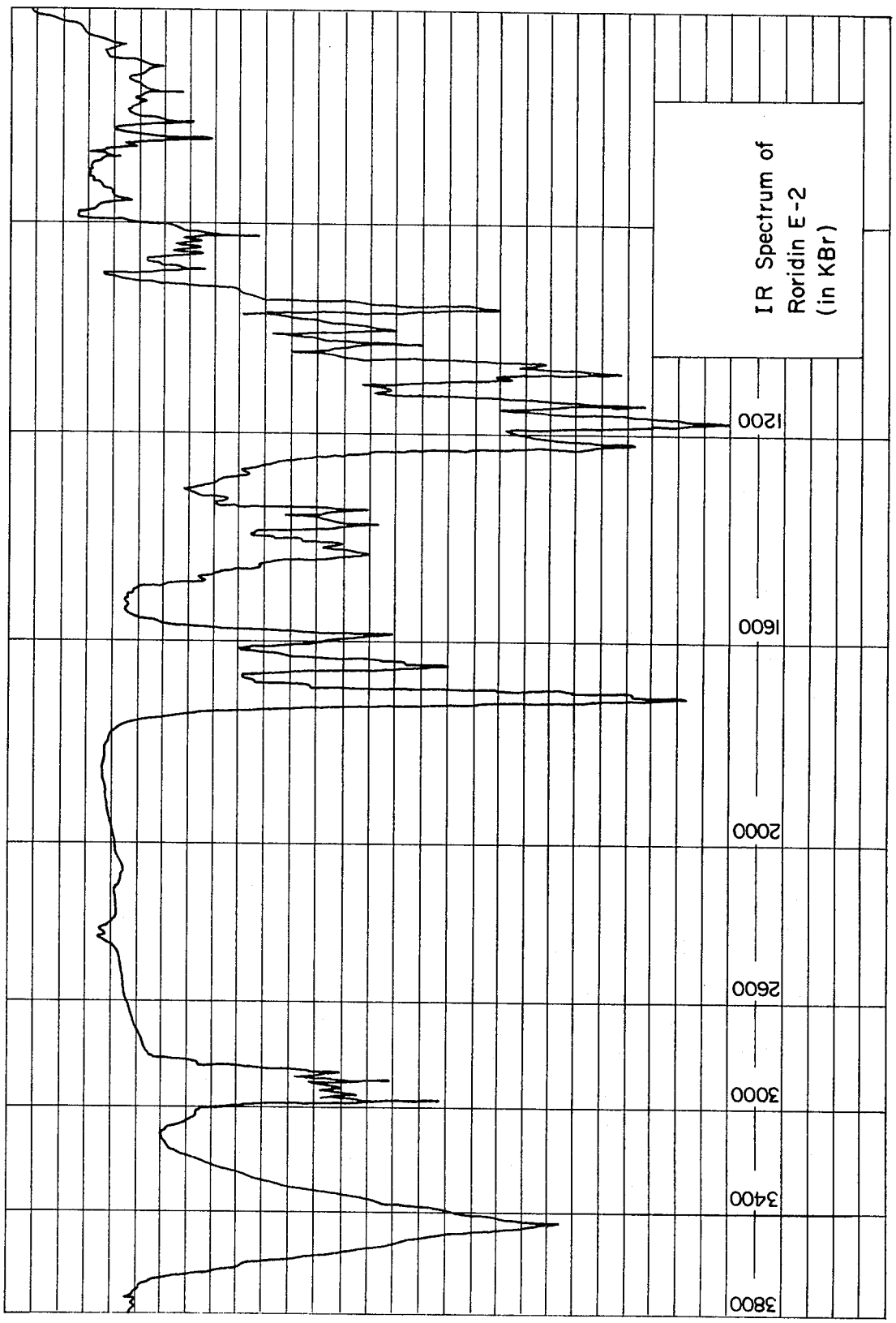
Figure 3:
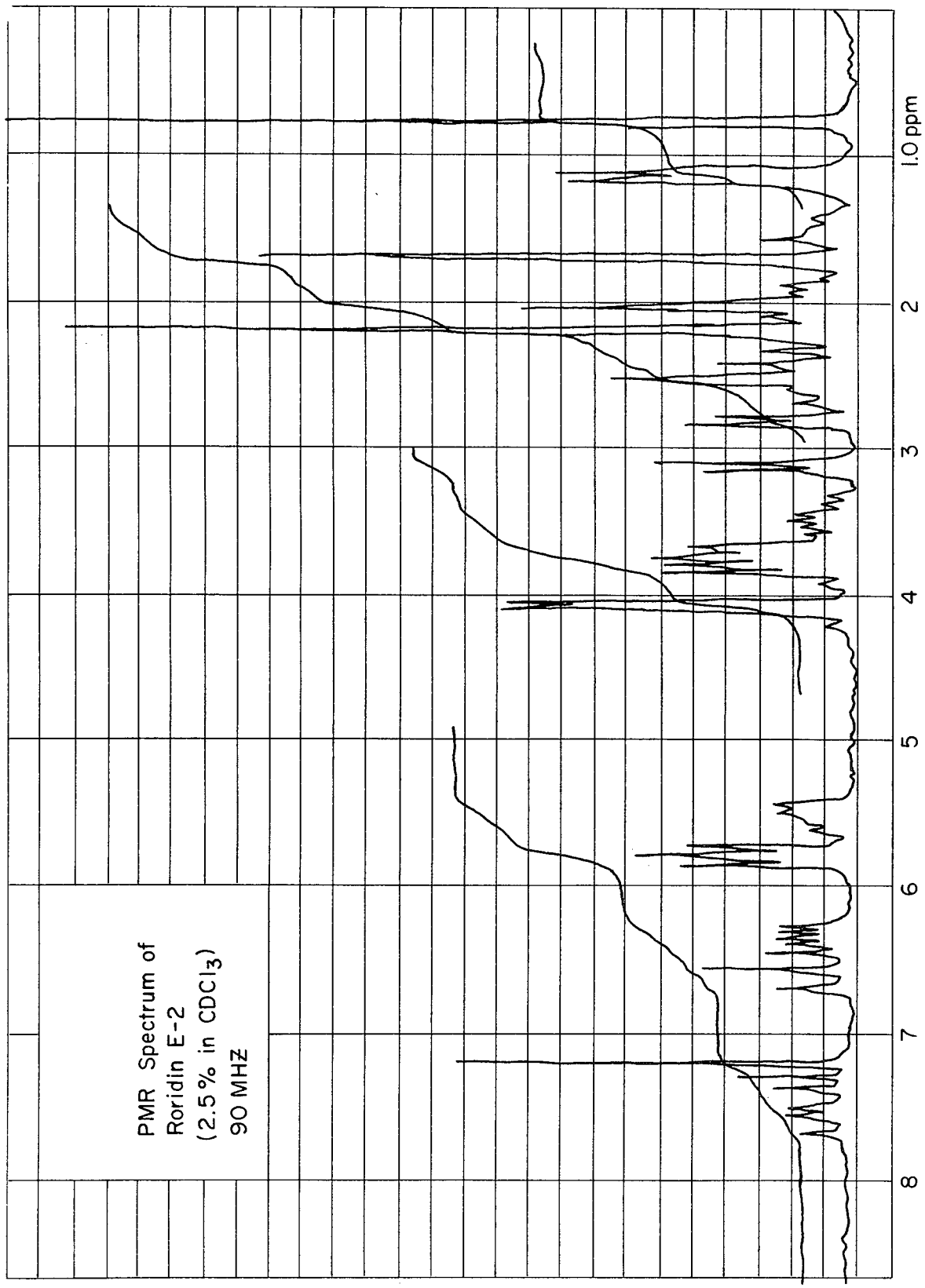

United States Patent [19]

Freckman et al.

[11] Patent Number: 4,463,182

[45] Date of Patent: Jul. 31, 1984

[54] ANTIBIOTIC RORIDIN E-2

[75] Inventors: William G. Freckman, Mt. Clemens; Zbigniew L. Jakubowski, St. Clair Shores; Richard H. Bunge, Mt. Clemens; James C. French, Ann Arbor; Lucia E. Balta, Harper Woods, all of Mich.

[73] Assignee: Warner-Lambert Company, Ann Arbor, Mich.

[21] Appl. No.: 919,023

[22] Filed: Jun. 26, 1978

[51] Int. Cl.³ .......................................... C07D 493/20
[52] U.S. Cl. .................................... 549/264; 424/279
[58] Field of Search ...................................... 260/340.2

[56] References Cited

PUBLICATIONS

B. Böhner et al., Helvetica Chimica Acta, vol. 48 (1965) pp. 1079-1087.
P. Traxler et al., Helvetica Chimica Acta, vol. 53 (1970) pp. 2071-2085.
Matsumoto et al., Jour. Antibiotics, vol. 30 (Aug. 1977) pp. 681-682.
Matsumoto et al., Tetrahedron Letters, vol. 47 (1977) pp. 4093-4096.

Primary Examiner—Norma S. Milestone
Attorney, Agent, or Firm—Krass & Young

[57] ABSTRACT

The present invention relates to roridin E-2 which is represented by Formula I and a process for the production of said compound:

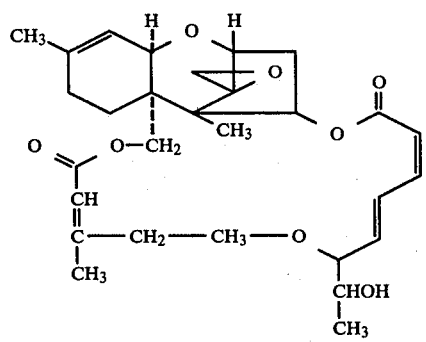

1 Claim, 3 Drawing Figures

ANTIBIOTIC RORIDIN E-2

SUMMARY AND DETAILED DESCRIPTION

The present invention relates to roridin E-2 which is represented by Formula I and a process for the production of said compound.

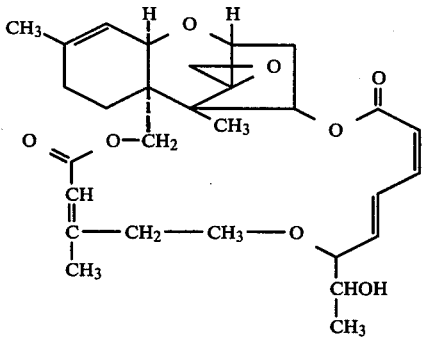

More particularly, the process relates to a fermentation process for the production of the compound of this invention using a roridin E-2 producing strain of the organism, *Myrothecium verrucaria*. In addition, the invention relates to pharmaceutical compositions containing the compound of the invention alone or in combination with other trichothecene derivatives in the treatment of neoplastic diseases.

HISTORY

In 1965, Christoph Tamm of the University of Geneva reported (*Helvetica Chimica Acta* 1965, 48, 1079–1087) the isolation and characterization of roridin E. In *Helvetica Chimica Acta* 1970, 53, 2071–2085, he assigned Structure II to roridin E which established it as a trichothecene derivative.

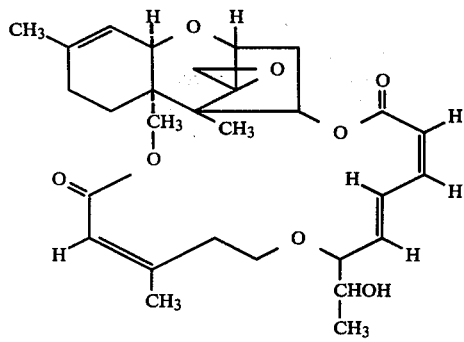

In a recent comprehensive review ("Progress in the Chemistry of Organic Natural Products," 1974, 31, 64–117), Dr. Tamm describes several trichothecenes related to roridin E. Among the compounds listed, no mention is made of a stereoisomer of roridin E nor, to our best knowledge, does a patent describing roridin E or any of its stereoisomers exist.

CULTURE CHARACTERIZATION AND FERMENTATION PROCESSES

In accordance with the present invention, roridin E-2 is produced by cultivating a selected roridin E-2 producing strain of the organism *Myrothecium verrucaria* under artificial conditions in a suitable nutrient medium until a substantial quantity of roridin E-2 is formed and isolating this compound in pure form by procedures described hereinafter.

A strain of *Myrothecium verrucaria,* suitable for the purpose of the invention, has been isolated from a sample of soil collected near Clewiston, Florida. Cultures of this organism (Parke-Davis Culture Bureau No. 06005) have been deposited with the United States Department of Agriculture, Northern Utilization Research and Development Division, Peoria, Ill., and are being maintained in their permanent culture collection as NRRL 11304. This microorganism is identified as a new strain of the fungus species *Myrothecium verrucaria* (Albertini and Schweinitz) Ditmar. The new strain corresponds morphologically to the description of this species by N. C. Preston (*Transactions Brit. Mycological Soc.* 1943, 26, 158) and J. C. Gilman ("Manual of Soil Fungi," Second Edition 1957, The Iowa State College Press, Ames, Iowa, page 398).

The antitumor compound, roridin E-2, is produced by the fungus during aerobic fermentation under controlled conditions. The fermentation medium consists of suitable sources of carbon, nitrogen, inorganic salts, and growth factors assimilable by the microorganism. Examples of carbon sources are various sugars such as cerelose, lactose, and maltose; starch, dextrin; corn meal; and glycerol. The normal quantity of the carbon source varies from about 0.5 to 6% by weight, but levels outside of this range can also be used.

The sources of nitrogen can be of organic, inorgaic, or mixed organic-inorganic in nature. The nitrogen sources that can be used in the culture medium are cottonseed meal, corn germ flour, soybean meal, corn steep liquor, distillers' solubles, peanut meal, fish meal, peptonized milk, and various ammonium salts. The normal amount added varies from 0.1 to 3%, but higher amounts are also acceptable.

The inclusion of certain amounts of minerals and growth factors in the fermentation medium is also helpful in the production of roridin E-2. Crude medium ingredients such as distillers' solubles, corn steep liquor, fish meal, yeast products, peptonized milk, and whey contain minerals and growth factors. However, inorganic salts such as potassium phosphate, sodium chloride, ferric sulfate, calcium carbonate, cobalt chloride, and zinc sulfate can be added to the fermentation medium.

The preferred method for producing roridin E-2 by *Myrothecium verrucaria* is by submerged fermentation. According to the embodiment of this invention, fermentation ingredients are prepared in solution and sterilized by autoclaving or steam heating. The pH of the aqueous medium is preferably between six to eight. The fermentation medium is cooled to a suitable temperature, between 20°–45° C., and then inoculated with the suitable culture. Fermentation is carried out with aeration and agitation. Optimum production of roridin E-2 is reached in about three to eight days.

In the submerged culture method, fermentation is carried out in shake-flask or in stationary-vat fermentors. In shake flasks, aeration is brought about by agitation of the flask which causes mixing of the medium with air. In the stationary fermentors, agitation is provided by impeller means such as disc turbine, vaned disc, open turbine, or marine propeller; and aeration is accomplished by injecting air or oxygen into the fermentation mixture.

The examples which follow illustrate the methods by which the product, roridin E-2, of this invention is obtained. The described processes are capable of wide variation, and any minor departure or extension is considered as within the scope of this invention.

EXAMPLE 1

Shake-Flask Production (Exp. Refs. #11223×40-33 and #11223×64-19)

The culture from a soil tube is transferred to a CIM-23 agar slant, incubated for 7–14 days at 28° C., and used as a source of inoculum or stored at 5° C. for not more than one month. A portion of the culture from the slant is used to inoculate an 18×150 mm test tube containing five ml of ARM 1515 seed medium.

| CIM-23 Slant Medium | |
|---|---|
| Amidex corn starch | 10 gm |
| N-Z Amine, type A | 2 gm |
| Beef extract (Difco) | 1 gm |
| Yeast extract (Difco) | 1 gm |
| Cobalt chloride.$6H_2O$ | 20 mg |
| Agar | 20 gm |
| Distilled water | 1,000 ml |

| ARM 1515 Medium | |
|---|---|
| Glucose, monohydrate | 20 gm |
| Soybean oil meal (44% extracted) | 10 gm |
| Proto-peptone #159 (Wilson) | 5 gm |
| $NH_4Cl$ | 2 gm |
| NaCl | 5 gm |
| $CaCO_3$ | 2.5 gm |
| Tap water | 1,000 ml |

Note: Adjust pH to 7.5 with NaOH before adding $CaCO_3$.

The seed tube is shaken at 30° C. on a gyratory shaker, 160 RPM, for six days.

Two 250-ml Erlenmeyer wide-mouth flasks, each containing 75 ml of ARM 1558, are inoculated with one ml per flask of the growth from the seed tube. These inoculated flasks are shaken at 30° C. for up to five days on a gyratory shaker, 224 RPM (2" throw). The fermentation beer after five days is colored tan with a thick oatmeal-like growth; pH is about 6.6; and a final residual sugar level of about 2% as tested with Lilly Tes-Tape®.

| ARM 1558 Medium | |
|---|---|
| Cerelose | 5.0% |
| Pharmamedia | 0.3% |
| Defatted corn germ flour | 0.1% |
| Soybean meal | 0.1% |
| $CaCO_3$ | 1.0% |
| $K_2HPO_4$ | 0.1% |
| $MgSO_4.7H_2O$ | 0.1% |
| NaCl | 0.05% |
| $FeSO_4.7H_2O$ | 0.0001% |
| Dow Corning antifoam "C" | 0.08% |
| Use tap water, no pH adjustment. | |

Production of trichothecenes in the fermentation broth is assayed vs. KB and L1210 tissue cell lines. An aliquot of the fermentation broth is mixed with growing cultures of KB and L1210 cells to give a final dilution of the fermentation broth of 1:100. Cytotoxic activity is expressed as the percent growth of the cells relative to the control (no fermentation broth added). A fermentation broth that gives percent growth values of 0–25% for KB and 0–50% for L1210 is considered active.

The cytotoxic activities of the fermentaton broths produced in shake flasks are as follows:

| | % Growth | |
|---|---|---|
| Flask # | L1210 | KB |
| I. (#11223 × 40-33) | 4 | 0 |
| II. (#11223 × 64-19) | 11 | 13 |

EXAMPLE 2

Fermentation in 200-Gal. Fermentors (PP 1264, PP 1265)

A. Seed Development

The culture from the soil tube is transferred to the CIM-23 slant and incubated at 28° C. for at least seven days. The microbial growths in two slants are scraped, suspended in distilled water, and used to inoculate a 30-liter seed fermentor. The seed fermentor is prepared by charging it with 16 liters of ARM 1558A medium, then autoclaved for 90 minutes at 121° C. and 15 PSI.

| ARM 1558A | |
|---|---|
| Cerelose | 3.0% |
| Pharmamedia | 0.3% |
| Defatted corn germ flour | 0.1% |
| Soybean meal | 0.1% |
| $CaCO_3$ | 1.0% |
| $K_2HPO_4$ | 0.1% |
| $MgSO_4.7H_2O$ | 0.1% |
| NaCl | 0.05% |
| $FeSO_4.7H_2O$ | 0.0001% |
| Use tap water, no pH adjustment. | |

The fermentor is cooled to about 30° C. and then inoculated with the microbial suspension prepared from the CIM-23 slants. The fermentor is stirred at 200 RPM and sparged with one volume per volume per minute (VVM) of air for 48 hours.

B. Production Fermentor

A 200-gal. fermentor is charged with 160 gal. of ARM 155S medium and sterilized by heating with steam for 40 minutes at 121° C. The fermentor is cooled to about 30° C. and then inoculated with about 16 liters of the microbial growth from the 30-liter seed fermentor. The inoculated fermentor is stirred at 190 RPM, sparged with about 1 VVM of air, and maintained at 3 PSIG pressure. Fermentation is carried out at 30° C. for about 120 hours; Dow Corning antifoam "C" is used to control foaming as required.

A second 200-gal. fermentor is inoculated following the same procedure. The activities of the fermentation broths at 120 hours vs. L1210 and KB cells are as follows:

| | % Growth | |
|---|---|---|
| Fermentor | L1210 | KB |
| PP 1264 | 6.8 | 0 |
| PP 1265 | 8.8 | 0 |

ISOLATION OF RORIDIN E-2

Two portions (428 liters and 409 liters) of fermentation beer, pH 6.6, prepared as described above, are treated with 48 kg of Celite 545 and filtered using a plate and frame filter press. The filtrate (832 liters) is extracted three times with approximately 190-liter portions of ethyl acetate. The organic extracts are combined and washed with 150 liters of water. The ethyl acetate layer (500 liters) is separated and concentrated in vacuo to 2.9 liters. This concentrated extract is then dried using anhydrous sodium sulfate, filtered, and the solvent removed in vacuo to leave approximately 300 g of an oily residue. This product, hereinafter referred to as residue A, can be processed in various ways to obtain roridin E-2. Two of these isolation methods are described in the following examples.

PURIFICATION METHODS

Example 1

A solution of approximately 42 g of residue A in 500 ml of ethyl acetate is extracted with 100 ml of 2M sodium hydroxide followed by three water washes using 100-ml portions of water each time. The ethyl acetate layer is then concentrated in vacuo to an oily residue which is reconstituted in 400 ml of methanol. The resulting solution is treated with 100 ml of water and extracted twice with 250-ml portions of petroleum ether (Phillips Petroleum Corp., b.p. 30°-60°). The lower aqueous methanol layer that remains is diluted with 100 ml of water and extracted three times with 150-ml portions of chloroform. The chloroform extracts are combined and concentrated in vacuo to an oily residue which is dissolved in 290 ml of benzene. This solution is filtered and added to a column containing 600 g of silica gel (Baker Chemical Co., particle size: 0.074-0.25 mm) packed in benzene. After the silica gel is washed with benzene, a mixture consisting of roridin E-2, verrucarin A, verrucarin J, and roridin E is eluted with benzene:-diethyl ether (75:25 by volume). This fraction is concentrated in vacuo to a viscous oil (about 10 ml) which is dissolved in 22 ml of diethyl ether, and the resulting solution is then treated with eight ml of petroleum ether and cooled to 5° C. to induce crystallization. The crystals are filtered off, washed with diethyl ether:petroleum ether (80:20) and dried; the weight of the product is 4.6 g.

A solution of the above product (4.5 g) in 30 ml of dichloromethane is applied to a column containing 400 g of silica gel (E. Merck, particle size: 0.063-0.20 mm) packed in dichloromethane. Elution is conducted using dichloromethane containing increasing amounts of ethyl acetate. Roridin E-2 is eluted with an 88:12 mixture of dichloromethane:ethyl acetate. These fractions are analyzed by high performance liquid chromatography (HPLC) (Waters Associates Inc., Milford, Mass.) on 3.9 mm (I.D.)×30 cm μPorasil® (silica gel) columns using a solvent system such as dichloromethane:-hexane:ethyl acetate:ethanol (170:170:70:2) with ultraviolet detection at 254 nm. The fractions which contain only roridin E-2 by HPLC are combined and concentrated to dryness in vacuo. The residue is crystallized from a 2:1 mixture of benzene:diethyl ether to afford 1.15 g of pure (>95%) roridin E-2.

Example 2

A solution containing approximately 35 g of residue A dissolved in 30 ml of dichloromethane is used as a charge for a Prep LC/System 500 apparatus which is available from Waters Associates Inc., Milford, Mass. Two PrepPak-500®/silica cartridges (5.7 cm×30 cm), each containing approximately 316 g of silica gel with a liquid void volume of about 460 ml, are used in series. After the sample is applied, the columns are washed first with 3.6 liters of dichloromethane to elute inert, nonpolar compounds. The eluant is then changed to 2.4 liters of dichloromethane:ethyl acetate (90:10) which elutes roridin H and verrucarin J. The next eluting solvent is 2.6 liters of dichloromethane:ethyl acetate (60:40) which yields two fractions: one containing verrucarin A and the other containing a mixture of roridin E and its isomer, roridin E-2. The columns are then eluted with four liters of ethyl acetate which removes other more polar trichothecene derivatives. After the columns are re-equilibrated with dichloromethane, they are ready to receive another 35 g charge of residue. This Prep-LC procedure was performed a total of six times with the same PrepPak-500®/silica cartridges with nearly the same resolution.

The fractionation procedures described here were monitored at all stages at 254 nm using HPLC on 3.9 mm (I.D.)×30 cm columns of μPorasil® with eluants such as dichloromethane:ethyl acetate (60:40) and dichloromethane:hexane:ethyl acetate:ethanol (170:170:70:2) or 3.9 mm (I.D.)×30 cm columns of μBondapak $C_{18}$® using methanol-water mixtures in the approximate ratio of 80:20.

The roridin E and roridin E-2 mixtures isolated from the six Prep LC/500 runs described above are combined; the weight of residue is about 40 g. This material, in approximately 3.5 g portions, is further resolved by a second Prep LC/System 500 chromatographic procedure using two PrepPak-500®/silica cartridges (5.7 cm×30 cm) in series and dichloromethane:ethyl acetate (65:35) as the eluant. Only one peak is detected by the refractive index monitor. A portion of the front of this peak is collected separately; the middle portion is recycled; and the back portion is collected separately. This procedure is repeated three times for each charge. At the end of this chromatographic separation, the front fractions are combined and afford a residue from which pure roridin E can be crystallized. The back fractions are combined and afford a residue which was crystallized from benzene:diethyl ether (1:4) and then dichloromethane:diethyl ether (1:5) to yield 2.35 g of pure (>95%) roridin E-2. The properties which define roridin E-2 as a new compound are listed below.

Properties of Roridin E-2:

m.p.: 184°-188° (uncorrected)

$[\alpha]_D$ −74° (0.85% in chloroform)

Ultraviolet Absorption Spectrum in Methanol (FIG. 1)

| λ max | $E^{1\%}_{1cm}$ | molar extinction (ε) |
|---|---|---|
| 221 nm | 475 | 24,415 |
| 259 nm | 326 | 16,756 |

Infrared Absorption Spectrum (KBr disk) (FIG. 2)

Principle absorptions at: 2980, 2900, 2860, 1712, 1655, 1600, 1440, 1380, 1360, 1230, 1185, 1150, 1090, 1040, 1010, 1000, 970, 890, and 830 reciprocal centimeters.

Proton Magnetic Resonance Spectrum in $CDCl_3$ (FIG. 3)

Principle signals at: (s=singlet, d=doublet, t=triplet, m=multiplet): 0.80s, 1.18d (J=6), 1.72s, 2.25d (J=1), 2.84d (J=4), 3.16d (J=4), 4.09d (J=12), 4.13d (J=12), 4.11d (J=12), 5.50m, 5.84m (complex;

area=3), 6.37dd (J=4, 8), 6.62t (J=11), 7.59dd (J=11, 15) parts per million downfield from tetramethylsilane.

Elemental Analysis and Molecular Weight

|  | % C | % H | Mol. Wt. |
|---|---|---|---|
| Calculated for $C_{29}H_{38}O_8$ | 67.68 | 7.44 | 514.6 |
| Found for roridin E-2 | 67.82 | 7.43 | 514.* |

*Molecular ion found in mass spectrum.

HPLC

μPorasil Col. #45721 (3.9 mm I.D.×30 cm)
System: dichloromethane:hexane:ethyl acetate:ethanol
170:170:70:2
Flowrate: 2 ml/min.
Ultraviolet detection at 254 nm.
Retention time of roridin E-2: Ca. 8 min.
Retention time of roridin E: ca. 7.5 min.
(Although day-to-day differences are encountered, a clear separation or roridin E-2 and roridin E, amounting to at least a 0.4 minute difference in retention times, is observed when these compounds, alone or as a mixture, are subjected to HPLC using the above conditions.)

| Antitumor Activity of Roridin E-2 Against P388 Lymphatic Leukemia in Mice: | |
|---|---|
| Dose (mg/kg/day) | T/C percent MST* |
| 6.25 | 166, 165 |
| 3.12 | 131 |
| 1.56 | 127 |

*T/C percent MST = median survival time in days of treated/control mice × 100. Values ≧ 125 are considered active. The test method used is based on that described in Cancer Chemother. Reports 3: 1-87 (Part 3), 1972.

| Antitumor Activity of Roridin E-2 Against B16 Melanocarcinoma in Mice: | |
|---|---|
| Dose (mg/kg/day) | T/C percent MST |
| 3.12 | 269, 202 |
| 1.56 | 157, 196 |
| 0.78 | 141, 190 |

The antibiotic roridin E-2 can be used for its antitumor activity in the form of pharmaceutical compositions containing roridin E-2 and a compatible pharmaceutically acceptable carrier. The compositions may also contain antimicrobial agents and other antitumor agents. The compositions may be made up in any pharmaceutical form appropriate for the route of administration in question. Examples of such compositions include solid compositions for oral administration such as tablets, capsules, pills, powders and granules, liquid compositions for topical or oral administration such as solutions, suspensions, syrups and elixirs and preparations for parenteral administration such as sterile solutions, suspensions or emulsions.

For use as an antitumor agent the compositions are administered in a dosage regimen such that tumor growth is inhibited. A suggested dosage regiment for use as an antitumor agent in mammalian species is 0.001 to 1.0 mg./square meter for a single daily parenteral treatment course with roridin E-2.

We claim:

1. Antibiotic roridin E-2 in substantially purified form represented by the formula

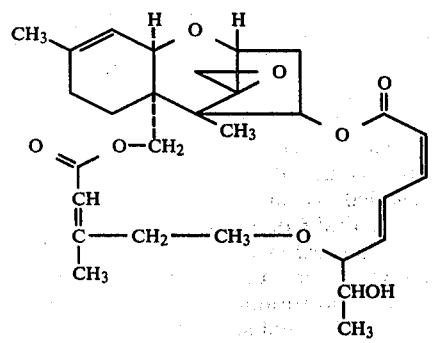

characterized by
(a) a proton resonance spectrum in $CDCl_3$ having principal signals at (s=singlet, d=doublet, t=triplet, m=multiplet): 0.80s, 1.18d (J=6), 1.72s, 2.25d (J=1), 2.84d (J=4), 3.16d (J=4), 4.09d (J=12), 4.13d (J=12), 4.11d (J=12), 5.50m,5.84m (complex; area=3), 6.37dd (J=4, 8), 6.62t (J=11), 7.59dd (J=11, 15) parts per million downfield from tetramethylsilane.
(b) melting point 184°-188° C. (uncorrected) and
(c) optical rotation $[\alpha]_D -74°$ (0.85% in chloroform).

* * * * *

UNITED STATES PATENT AND TRADEMARK OFFICE
CERTIFICATE OF CORRECTION

PATENT NO. : 4,463,182
DATED : July 31, 1984
INVENTOR(S) : Freckman et al.

It is certified that error appears in the above-identified patent and that said Letters Patent is hereby corrected as shown below:

On the title page in the abstract, delete the formula and substitute therefor:

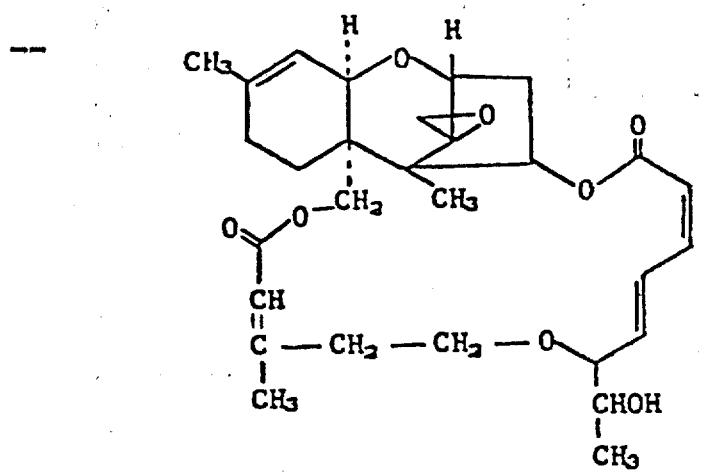

Signed and Sealed this

Twenty-third Day of April 1985

[SEAL]

Attest:

DONALD J. QUIGG

Attesting Officer    Acting Commissioner of Patents and Trademarks